United States Patent [19]

Thomas, Jr. et al.

[11] Patent Number: 5,006,460

[45] Date of Patent: Apr. 9, 1991

[54] METHOD FOR MEASURING DNA DAMAGE IN SINGLE CELLS

[75] Inventors: Charles A. Thomas, Jr., La Jolla; Eric A. Thomas, Solana Beach, both of Calif.

[73] Assignee: Pantox Corporation, San Diego, Calif.

[21] Appl. No.: 198,995

[22] Filed: May 26, 1988

[51] Int. Cl.$^5$ .................. C12Q 1/68; G01N 33/533
[52] U.S. Cl. ........................... 435/6; 435/29; 435/91; 435/803; 436/501; 436/519; 436/543; 436/177; 436/178; 436/815; 436/825; 536/27; 935/19; 935/77
[58] Field of Search ............ 435/6, 29, 91, 803; 436/501, 519, 543, 177, 178, 815, 825; 536/27; 935/19, 77

[56] References Cited

U.S. PATENT DOCUMENTS 4,407,942 10/1983 Birnboim .................. 435/6

FOREIGN PATENT DOCUMENTS 62-008053 1/1987 Japan .
62-209339 9/1987 Japan .
673247 7/1979 U.S.S.R. .
1152369 3/1986 U.S.S.R. .

OTHER PUBLICATIONS

Roti Roti et al., (1987), Cytometry, 8:461–467.
Cook et al., (1975), J. Cell Sci., 19:261–279.
Cook et al., (1976), J. Cell Sci., 22:303–324.
Kohn et al., (1976), Biochemistry, 15:4629–4637.
Rydberg, B. and Johanson, K. J., (1978), Estimation of DNA Strand Breaks in Single Mammalian Cells. in DNA Repair Mechanisms, Hanawald, P. C. and Friedberg, E. C., eds., pp. 465–468.
Vogelstein et al., (1980), Cell, 22:79–85.
Pardoll et al., (1980), Cell, 19:527–536.
Maniatis et al., (1982), *Molecular Cloning: A Laboratory Manual*, Cold Spring Harbor Laboratory, N.Y., pp. 55–74.
Birnboim, (1983), Methods in Enzymology, 100:243–255.
Serwer, (1983), Electrophoresis, 4:375–382.
Storer et al., (1984), Analytical Biochemistry, 142:351–359.
Ostling et al., (1984), Biochemical and Biophysical Research Communications, 123:291–298.
Cuiffo et al., (1985), Journal of Free Radicals in Biology & Medicine, 1:139–144.
Flickinger et al., (1986), Cell Differentiation, 19:59–71.
Murray et al., (1987), Analytical Biochemistry, 160:149–159.
Cathcart et al., (1984), Proc. Natl. Acad. Sci., USA, 81:5633–5637.
Adelman et al., (1988), Proc. Natl. Acad. Sci., USA, 85:2706–2708.
Singh et al., (1988), Experimental Cell Research, 175:184–191.

*Primary Examiner*—Robert A. Wax
*Assistant Examiner*—Ardin H. Marschel
*Attorney, Agent, or Firm*—Lahive & Cockfield

[57] ABSTRACT

A method of measuring chain breakage in the DNA of a eucaryotic cell is disclosed. This method includes (a) contacting the cell with a stripping solution that lyses and solubilizes the cell without denaturing its DNA, thereby forming a nucleoid having a halo, (b) measuring the width of the halo, and (c) determining the number of chain breaks from the measured width. The halo includes at least one loop of undenatured DNA, and has a width related to the number of DNA chain breaks in the loop. The cell to be examined may be adhered to a support prior to its contact with the stripping solution. The number of DNA chain breaks can be determined by comparing the measured width of the nucleoid halo with a reference value.

37 Claims, 6 Drawing Sheets

HELA CELL NUCLEOIDS WITH HALOS EXPANDED (bar = 10 microns)

*HELA CELL NUCLEOIDS WITH HALOS EXPANDED (bar = 10 microns)*

*HELA CELL NUCLEOIDS WITH HALOS CONTRACTED (bar = 10 microns)*

METHOD FOR MEASURING DNA DAMAGE IN SINGLE CELLS

BACKGROUND OF THE INVENTION

This invention relates to the detection of DNA damage in eucaryotic organisms, and more specifically, to methods which quantitate the level of DNA chain breakage in individual cells.

DNA is a relatively fragile molecule which can be easily damaged in vivo by a number of different elements. For example, bending or shear forces can result in single-strand and double-strand breaks; a local pH change may cause the loss of constituent purine bases; chemical agents from the environment may modify one or more bases; and X-rays or ultraviolet (UV) radiation may bring about a chemical change in a base. Such changes in DNA may also be the result of radicals generated by normal metabolism. This kind of damage may be exacerbated by malnutrition, various toxins, or a subclinical disease state.

Nevertheless, DNA has the capacity to undergo faithful replication. The integrity of the information content of DNA is protected in large measure by enzymes capable of accurately repairing certain kinds of damage or defects in one strand of DNA so long as the other strand, which contains the complementary information, is intact.

Chromosomal DNA in mammalian cells is generally a continuous double helix over most of its length. For this reason it may be supercoiled Bases which are damaged, altered, or mismatched are subject to an intracellular repair mechanism called the excision-repair process, which involves the sequential action of several enzyme activities illustrated in FIG. 1 for the case of one special kind of damage. The defect is initially detected by a DNA polymerase which has a patrolling function, and which makes an incision on one side of the defect, thereby breaking one of the two polynucleotide chains which form the double helix. Following the removal of the damaged base(s), as well as many of the surrounding nucleotides, resynthesis of the DNA strand occurs using the undamaged, complementary chain as a template. The defective fragment is enzymatically excised, and the remaining nick is then religated to restore the continuity of the strand and the structure of the double helix. Thus, DNA damage of many types results in a transient strand-breakage which is part of the repair process. The repaired DNA is "as good as new" provided that the excision-repair process proceeds normally.

However, perfect repair does not always occur. Incorrect nucleotides are inserted at a low frequency, thereby resulting in somatic mutations that are perpetuated by each round of cellular division. The measurement of the rate of cellular DNA damage has assumed increasing importance because it appears that the accumulation of such damages, or resulting somatic mutations, can render the genome even more vulnerable to subsequent mutation, and may play a central role in degenerative diseases, cancer and aging.

Since different types of damage result in transient strand breakage, the incidence of strand breakage is an integrated measure of DNA damage. The speed of the cut, resynthesis, and religation processes limit the time over which the damage events may be registered as strand-breaks, but the repair process as a whole may be inhibited or may not exist at all in certain types of cells. Thus, the "not yet repaired window may be of variable width depending on cell type.

The importance of strand breakage, particularly as a consequence of radiation, has stimulated a great deal of work leading to measures of DNA damage. The procedures for damage assessment developed in the prior art include: alkaline sedimentation, alkaline unwinding (Storer et al. (1984) Anal. Biochem 142:351–359), filter elution (Kohn et al. (1976) Biochem. 15:4629–4637; Murray et al. (1987) Anal. Biochem. 160:149–159), and nucleoid sedimentation (Cuiffo et al. (1985) J. Free Radicals in Biol. Med. 1:139–144). However, these methods require about $10^6$ cells, and do not represent potential methods for determining low level radical damage in intact animals or humans.

An estimation of DNA damage has been calculated from a determination of the amounts of oxidized bases and nucleotides excised from the DNA by the excision-repair process and subsequently collected in the urine (Carthcart et al. (1984) Proc. Natl. Acad. Sci. USA 81:5633–5637; Adelman et al. (1988) Proc. Natl. Acad. Sci. USA 85:2706–2708). Using this method, it has been determined that most cells are subject to a surprisingly high rate of damage. Moreover, this rate of damage is proportionately higher in mammals having higher metabolic rates.

However, from an experimental and diagnostic point of view, it would be highly desirable to be able to measure the damage that an individual cell of identifiable type has sustained, since the rate of damage is likely to be variable depending on the individual donor, cell type, and cell age as well as state of activation. Earlier work on single cells has been based upon the lysing cells embedded in agarose under alkaline conditions, (Rydberg et al. (1978) *DNA Repair Mechanisms*, Hanawold and Friedberg, eds. pp. 465–468), followed by electrophoresis under neutral or alkaline conditions (Ostling et al. (1984) Biochem. Biophys. Res. Commun. 123:291–298; Singh et al. (1988) Expt. Cell Res. 175:184–191). The extent of DNA damage is determined by comparing the migration pattern of the DNA with that of control DNA. These methods are sensitive, but have the drawback that the embedding procedure requires time, loses track of individual cells, denatures the DNA, and changes the conditions of their surface contacts. Pardoll et al. (Cell (1980) 19:527–536) and Cook et al. (J. Cell Sci. (1976) 22:303–324) describe the formation of a nuclear matrix structure composed mainly of undenatured DNA, but neither suggest being able to determine the presence or extent of DNA damage from such a structure.

Therefore, it is an object of the invention to provide a simple and efficient method of determining the extent and rate of DNA damage occurring in an animal or human.

It is also an object of the invention to provide a simple procedure to measure the incidence of DNA chain breakage in an individual cell.

It is another object of the invention to provide a sensitive method for detection of DNA chain breakage which can be applied before the natural repair and religation process is completed.

These and other objects and features of the invention will be apparent from the description, drawings, and claims which follow.

SUMMARY OF THE INVENTION

Methods are disclosed herein for the measurement of DNA chain breakage in a eucaryotic cell. For the first time, we have applied halo extension, or width, as a quantitative assessment of DNA damage. It has been discovered that the halo width of a nucleoid is related to the number of unrepaired chain breaks the DNA constituting the halo has sustained prior to nucleoid formation.

The term "chain breakage" is used herein to describe a cut or interruption in either a single or double strand of DNA making up the double helix. A "nucleoid" refers to the structure which remains after a cell has been lysed and solubilized with a stripping solution, leaving mainly DNA and residual nuclear proteins. The nucleoid has a relatively dense core portion and a less dense periphery, or "halo", disposed about the core and consisting of loops of double stranded DNA (which are supercoiled if uninterrupted), and which extend outward from the core. The number of chain breaks can be determined by comparing the measured width of the halo with a reference value.

The cell from which the nucleoid is made can be any eucaryotic cell, or a cell having a nucleus with DNA contained therein. In one aspect of the invention, the cell is a mammalian cell which may have substantially low DNA repair abilities, such as a lymphocyte, or which may have its DNA abilities inhibited, for example, by a DNA polymerase inhibitor.

To form a nucleoid, according to the invention, the cell is contacted with a stripping solution which solubilizes and lyses it without denaturing its DNA. The pH of this stripping solution is in the range of about 6.0 to 9.0, and in one preferred embodiment, has a pH of about 8.0.

This stripping solution contains a detergent which may be nonionic or ionic. For example, it may be the nonionic detergent polyoxylthylene ether or the ionic detergent sodium lauryl sulfate. In one aspect of the invention, the stripping solution contains about 0.50 to 0.75% polyoxyethylene ether with about 0.66% being preferable.

The stripping solution also contains a salt. Salts useful in the stripping solution may be a salt of an alkali metal such as NaCl, and of a bivalent cation such as $Mg^{+2}$ and $Ca^{+2}$. In a preferred embodiment of the invention, the stripping solution contains about 2 M NaCl, about 10 and about 0.5 mM $Ca^{+2}$. It may additionally include a sugar such as sucrose present at about 5 to 10%, but preferably at about 7.3% by weight.

Nucleoid halos formed from DNA that contains no single or double chain breaks always appear contacted exposed to 50 µg/ml EB (one of many possible intercalating fluorochromes). The halo expands if chain breaks are present.

The width of the halo has been shown to provide a measure of DNA damage.

The cell whose DNA damage is to be measured may undergo various treatments before being stripped. For example, the cell may be pretreated with a DNA repair inhibitor. The cell may also be adhered to a support. In one aspect of the invention, adherence is accomplished by culturing the cell on a glass cover slip. Alternatively, the cell may be adhered to the support via a substance which is capable of binding the cell such as a cell surface receptor or antibody. In this embodiment, the support is pretreated with such a substance prior to its contact with the cell to be adhered.

The method of the invention may further include the step of increasing the length of the loops of undenatured DNA making up the halo prior to the nucleoid forming step. The length may be increased by exposing the loop to a solution containing urea, proteases, or by exposure to an electrostatic or hydrodynamic field.

In a preferred aspect of the invention, the step of determining the number of chain breaks from the measured width is executed by (1) adhering the cell to be examined to a light transmissive support, (2) stripping it, (3) staining the resulting nucleoid with a fluorochrome capable of intercalating between the base pairs of undenatured DNA, (4) illuminating the nucleoid with light capable of exciting the fluorochrome, and then (5) determining the width of the halo. The fluorochrome, such as ethidium bromide, propidium diiodide, or acridine orange, may be applied to the nucleoid in a solution having a pH of about 6.0 to 8.0, but preferably of about 7.5. The staining solution may further include at least one salt and a buffer. In a preferred aspect of the invention, the staining solution contains about 2 M NaCl, about 5 mM $Mg^{+2}$, about 10 mM Tris, and up to about 100 ug/ml ethidium bromide.

The illuminating step may be carried out by shining a light having a wavelength of about 510–560 nm (green light) on the stained nucleoids. In one embodiment of the invention, both the illuminating and measuring steps are carried out with the use of an epifluorescence microscope, having means therein to measure the width of the nucleoid halo.

DESCRIPTION OF THE DRAWINGS

The foregoing and other objects of this invention, the various features thereof, as well as the invention itself, may be more fully understood from the following description, when read together with the accompanying drawings, in which.

DESCRIPTION OF THE INVENTION

The supercoiling of covalently closed circular Plasmid DNA molecules is now well-understood. A single (or double) chain breakage relaxes the supercoiled plasmid thereby allowing it to expand. This is true for covalently joined plasmid DNAs of even very large size. Thus, the relaxation of supercoiled DNA is a measure of chain breakages, the sensitivity of which depends on the number of base pairs in the supercoiled structure.

Figure 1:
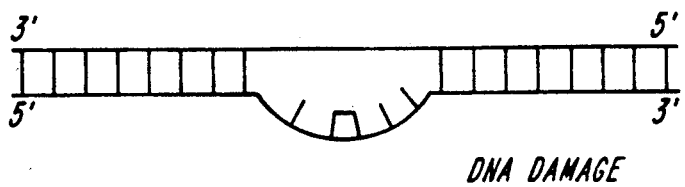
FIG. 1 is a diagramic representation of the repair of double-stranded DNA by the excision-repair process for one kind of DNA damage.
Figure 1:
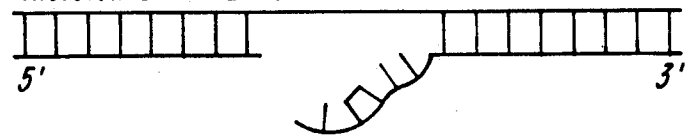
Figure 1:
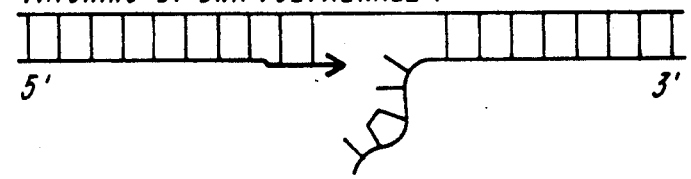
Figure 1:
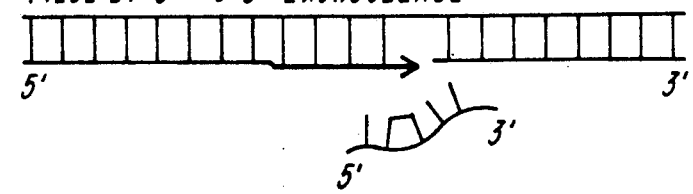
Figure 1:
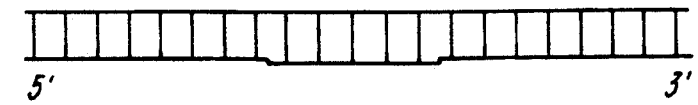
Figure 2:
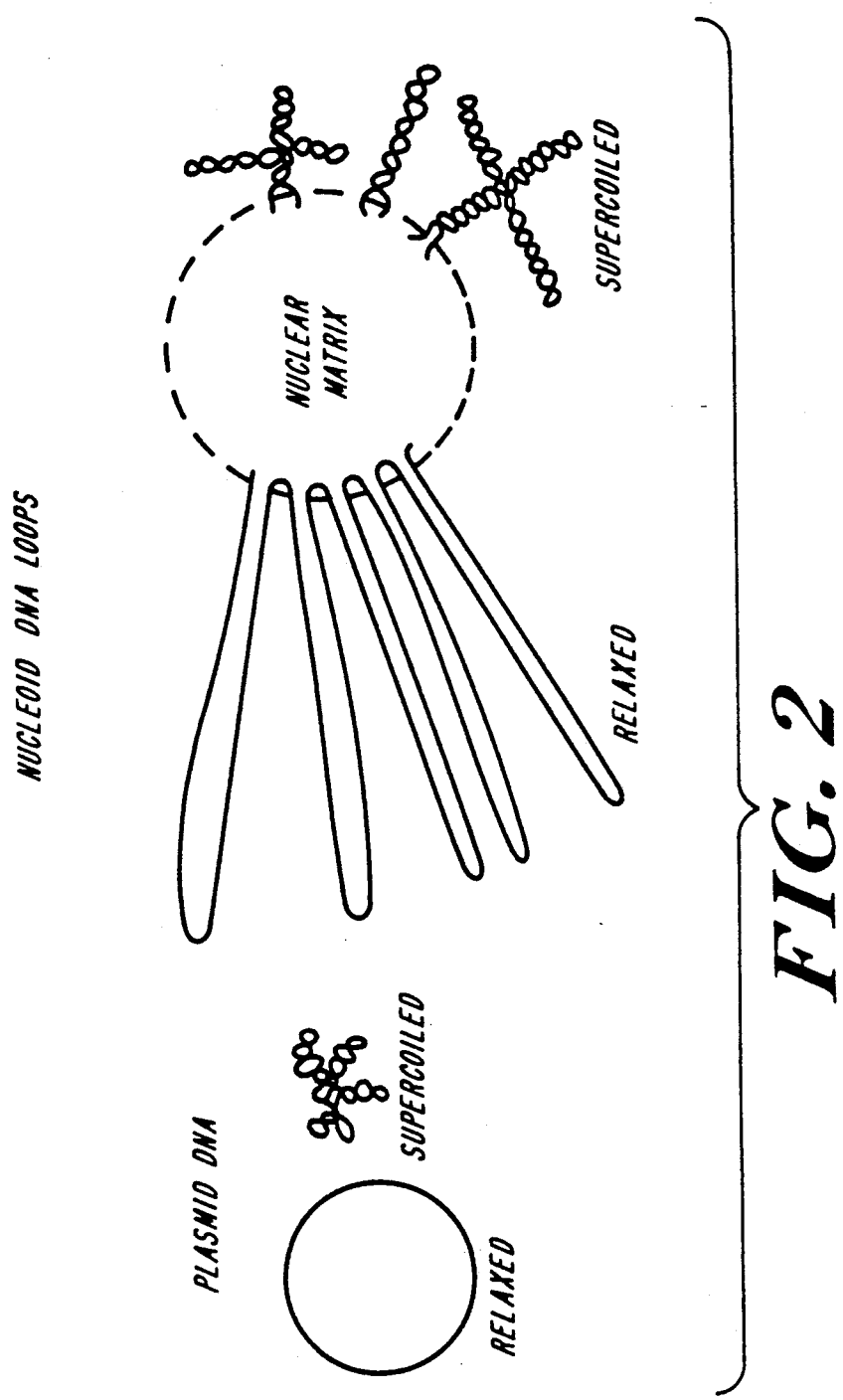
FIG. 2 is a schematic representation of nucleoid halo loops and plasmid DNA in relaxed and supercoiled condition. Not shown are the loops which are locally entangled with one another.

Supercoiled nuclear DNA can be observed in the form of nucleoids. Nucleoids are formed by the treatment of cells at neutral pH with ionic or nonionic detergents and high salt which remove the lipid membranes and most of the nuclear proteins. The free DNA remains in the form of long, probably tangled loops that are anchored in the residual nuclear matrix and possibly other places as well. This anchoring prevents free rotation of the double helix, and the nucleoid loops extending from the core can be supercoiled for that reason. Generally, the nucleoid includes a relatively high density core of supercoiled DNA and residual matrix proteins surrounded by a peripheral portion of extended DNA loops having less density than the core. FIG. 2 shows a schematic representation of a nucleoid having a core and a plurality of relaxed and supercoiled DNA loops extending peripherally from the core.

For nucleoids formed from cells grown on glass coverslips, the nuclear matrix remains attached to the coverslips, and the surrounding DNA can be stained with ethidium bromide (EB) or other fluorochromes. When illuminated with light of a particular wavelength, the core portion of the nucleoid is relatively bright while the peripheral region forms a relatively less bright "halo". Under these conditions the nucleoids can be directly observed with a fluorescence microscope, permitting measurement of the halo width.

When the cell is irradiated with gamma rays prior to nucleoid formation, the halo generally expands, the fractional expansion of the halo being roughly proportional to the dose of radiation. Exposure to ultraviolet irradiation (UV) maximally expands the halos.

Halo expansion can be quantitated by comparison with a reference value. For example, supercoiled plasmid DNAs of known size can be added to the solution containing the cell and treated simultaneously in the same way as is the cell. Their responses to treatment may then be compared.

Generally, DNA damage incurred by living cells is repaired with time, thereby reducing nucleoid halo size. To examine the damage, various DNA synthesis inhibitors can be added to cells prior to nucleoid formation to arrest DNA repair, thereby increasing nucleoid halo size. This step may therefore increase the sensitivity of the DNA chain breakage measurement made in accordance with the present invention.

The following examples are by way of illustration, without limiting the scope thereof.

EXEMPLIFICATION

Cell Culture:

Cell lines V79-171 (a Chinese hampster line obtained from Dr J. Ward), HeLa, and human primary foreskin fibroblasts are cultured separately in 25 mm plastic flasks at 37° C. in 5% $CO_2$ in MEM growth medium containing 10% heat-inactivated fetal bovine serum. The medium is replaced at intervals of 3 days. As the cells approach confluence, the medium is replaced by Hank's Balanced Salt Solution containing 0.25% trypsin and incubated for 5 min. After resuspension by vigorous pipetting, aliquots are transferred to new flasks or petri dishes having steam sterilized conventional microscope coverslips (22 mm×22 mm×0.1 mm) therein. Cells attach to the glass coverslips and grow such that the coverslip supports the cells on one of its principal surfaces.

Lymphocytes:

Rat lymphocytes were obtained from a few drops of blood taken from the tail.

Preferably, peripheral lymphocytes are adhered to the conventional microscope coverslips (22 mm×22 mm ×0.1 mm). Adherence can be facilitated by pretreatment of the glass coverslips with substances which have cell immobilization properties such as various cell binding substances albumin and alum, or specific antibodies. In addition, the lymphocytes can be centrifuged onto coverslips to assure their combination with the specific antibody.

A small circular retaining ring is mounted onto the coverslip with molten paraffin. A sample of blood is placed within the ring and placed into a swinging bucket centrifuge where the coverslip is subjected to sufficient gravitational acceleration to fix the leukocytes to the slip.

Two small rectangular coverslips (11 mm×22 mm×0.1 mm) are placed 3 mm apart on a conventional microscope slide. A drop of growth medium is placed in the rectangular space between the small coverslips. The above-described cell-bearing coverslip is placed on the two smaller coverslips with the cell-bearing surface facing the underlying microscope slide, thereby forming a chamber open at each end and bounded by portions of the three coverslips. Filter paper is Positioned at one end of the chamber for absorption of fluids drawn through the chamber. Temperatures in the range of 10° to 80° C. are maintained by a warm air hair drier, and monitored by a thermometer on the stage.

Microscopy:

A conventional Zeiss phase-contrast microscope (Standard RA) is equipped with an epifluorescence adaptor consisting of filters and dichroic mirror. A high intensity mercury source (HBO 200W/4) is directed into the epiillumination system. The primary excitation energy is the mercury emission at 510–560 nm (green). Observations are made through an interference filter passing 590 nm (red) light. This system permits simultaneous observation of nucleoids by fluorescence and by phase contrast microscopy.

Alternatively, the nucleoid halos may be observed by photon counting Cameras. The resulting digital images may then be processed by morphometric analysis programs that promise a substantial automation of the entire procedure.

Preparation of Nucleoids:

A small drop of stripping solution, containing 0.66% Triton X-100 (polyoxylthylene ether), 2 M NaCl, 5 mM $Mg^{++}$, 0 5 mM $Ca^{++}$, 7.3% sucrose, and 10 mM Tris pH 8.0, is introduced to the chamber at one of its open ends. Filter paper is positioned at the opposite end of the chamber to draw the introduced solution therethrough. The staining solution, containing 2 M NaCl, 5 mM $Mg^{++}$, 10 mM Tris pH 7.5, and from 0 to 100 µg/ml EB, is then similarly applied. Observations are performed by phase contrast and fluorescence microscopy.

Measurement of Halo Extension:

Halo measurements are then made in the resultant nucleoids in the chamber using the microscope, as equipped with a graticule in one eyepiece, where the image plane is coincident with the plane of the graticule. All measurements are made under reduced intensity. The halo size for a nucleoid is measured from the peripheral edge of the nuclear matrix core to the peripheral edge of the halo.

Figure 3A:
FIGS. 3A and 3B are fluorescence photomicrographs of HeLa cell nucleoids treated with (A) 5 µg/ml EB, causing the nucleoid halos to expand, and with (B) 100 µg/ml EB, causing the halos to contract.
Figure 3B:
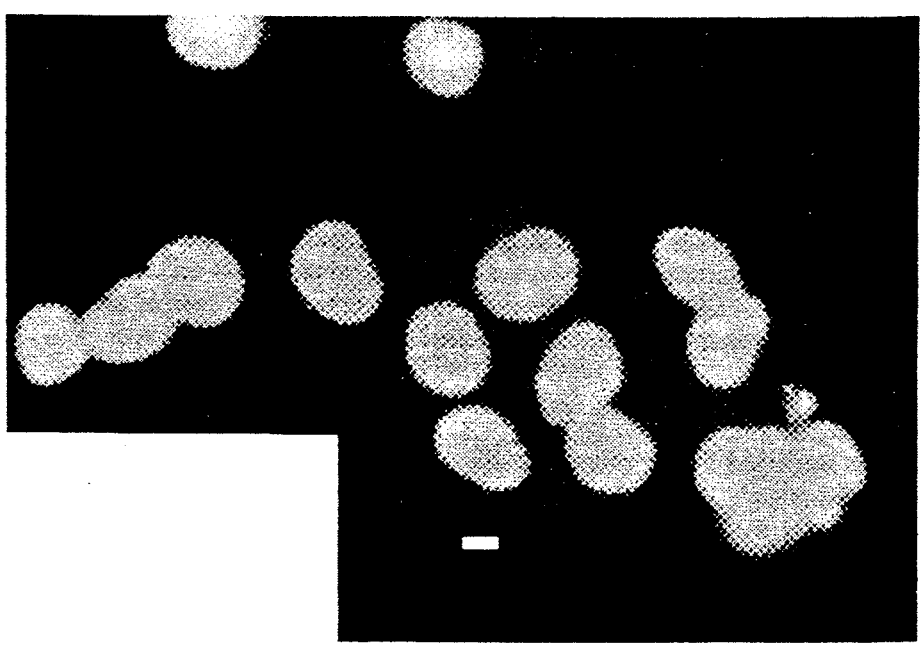
Figure 4:
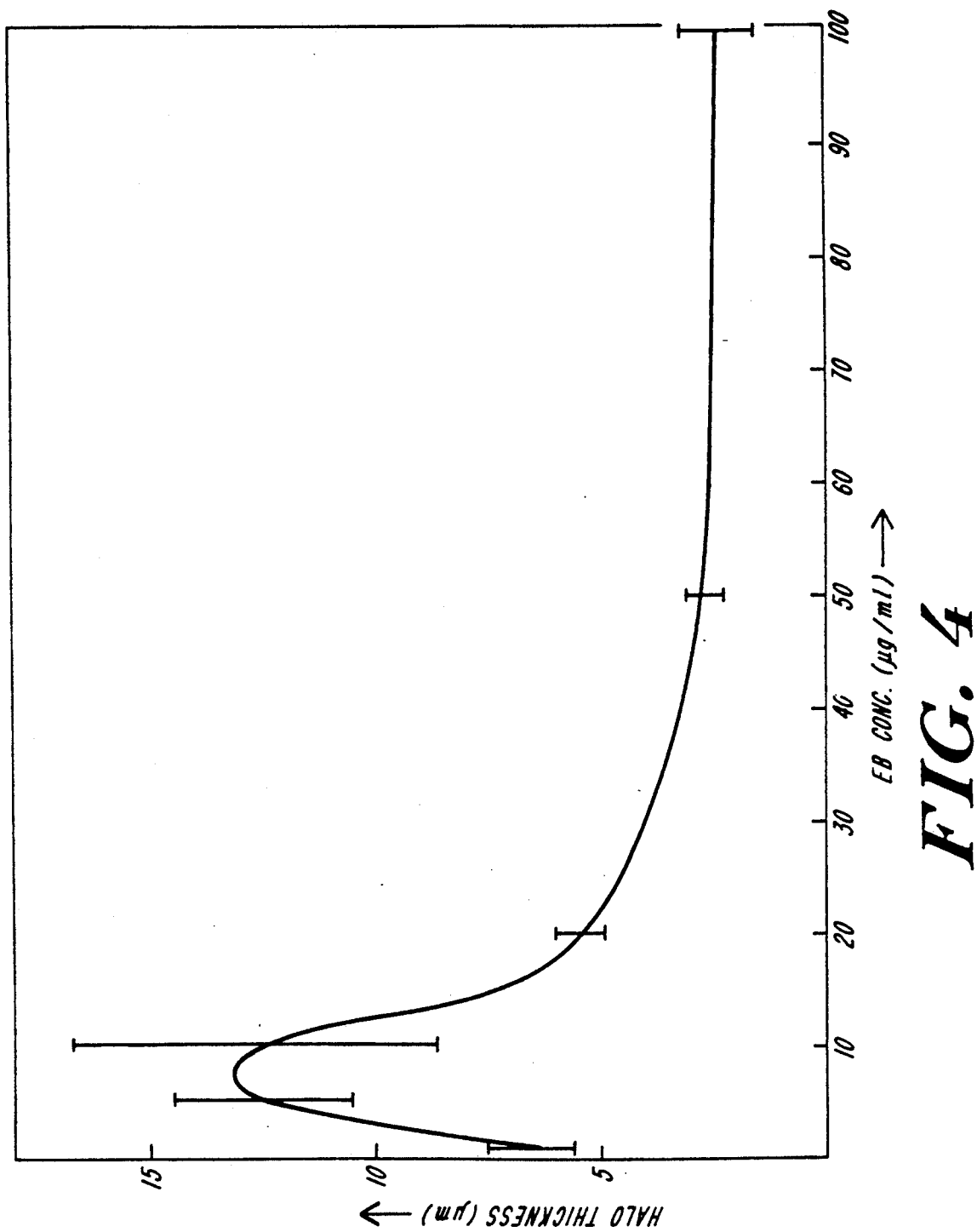
FIG. 4 is a graph of the relationshiP between halo thickness and ethidium bromide concentration.

The nucleoids formed from the cells in the chamber, as defined above, appear as shown in FIGS. 3A and 3B, provided that no chain breaking damage has occurred in the halos. The extension of the halos depends on the concentration of EB. For example, in the presence of 5 $\mu$g/ml EB, HeLa nucleoids are expanded (FIG. 3A); in the presence of 100 $\mu$g/ml EB, they are contracted (FIG. 3B). FIG. 4 demonstrates the relationship between halo size and EB concentration. The characteristic increase, and then decrease in halo extension as the EB concentration increases, is evidence that the halos are constructed of DNA supercoils. Each nucleoid is measured at least twice, and the measurements from 8 to 10 nucleoids are averaged for each point. A maximum thickness is produced at 5–10 $\mu$g/ml EB in 2 M NaCl.

Figure 6:
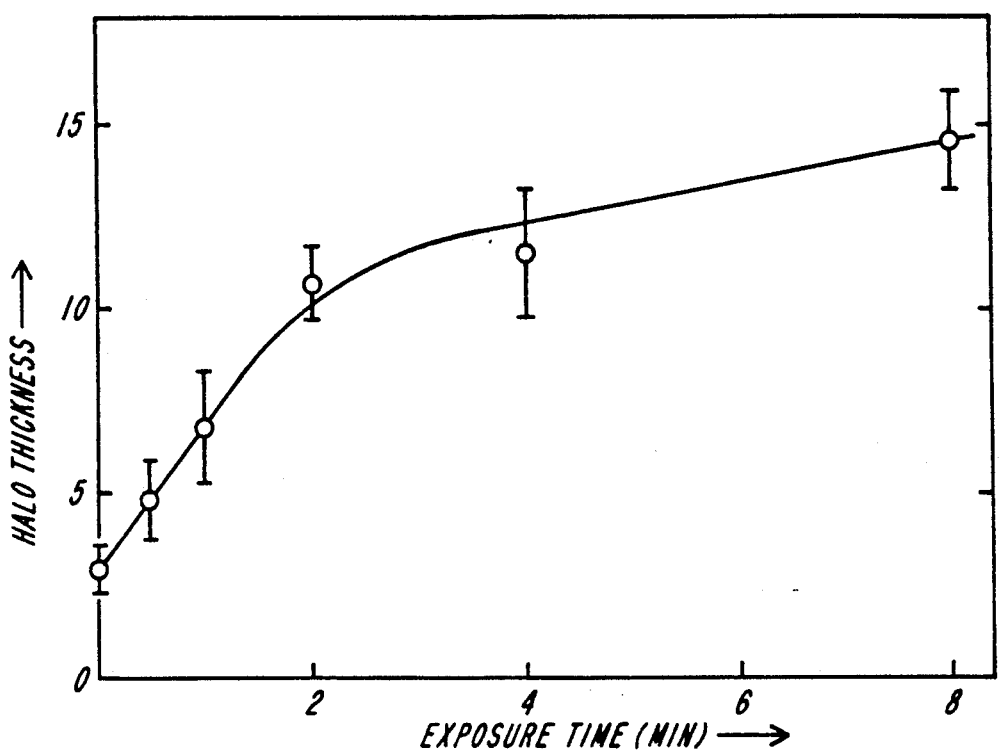
FIG. 6 is a graph of the relationship between halo thickness and the time nucleoids are exposed to green light in the presence of EB. Each point results from a different cell-chamber preParation.

In addition, the DNA loops of the halos can be relaxed and extended by DNAase treatment, Photodynamic chain nicking, or $H_2O_2$ treatment all in a dose-dependent manner. For example, FIG. 6 shows the dose-dePendent relationship between halo thickness and exPosure (time) to green light in the Presence of 50 $\mu$g/ml EB.

Gamma Irradiation:

The assembled microscope slides with nucleoids bathed in a solution containing the plasmid DNA in 10 mM Tris (pH 7.5), 2 are exposed at room temperature to a $Co^{60}$ source at an appropriate distance to keep the exposure time greater than 1.6 min and less than 13 min. The solution containing the plasmid is then removed for gel analysis while the nucleoids are stained with EB in the same buffer and the halos measured. Growing cells are irradiated in growth medium at room temperature.

Exposure of Growing Cells to Chain-Breaking Treatments:

V-79 cells growing in a coverslip chamber are chilled to 0° and treated with 200 $\mu$M $H_2O_2$ in growth medium. After 10 min, fresh growth medium is applied and incubation continued are at either 0° C. or room temperature (RT) and in medium containing inhibitors or not. Three inhibitors are used simultaneously: 40 mM hydroxyurea; 100 $\mu$M 5-fluorodeoxyuridine (5FdU).

Figure 7:
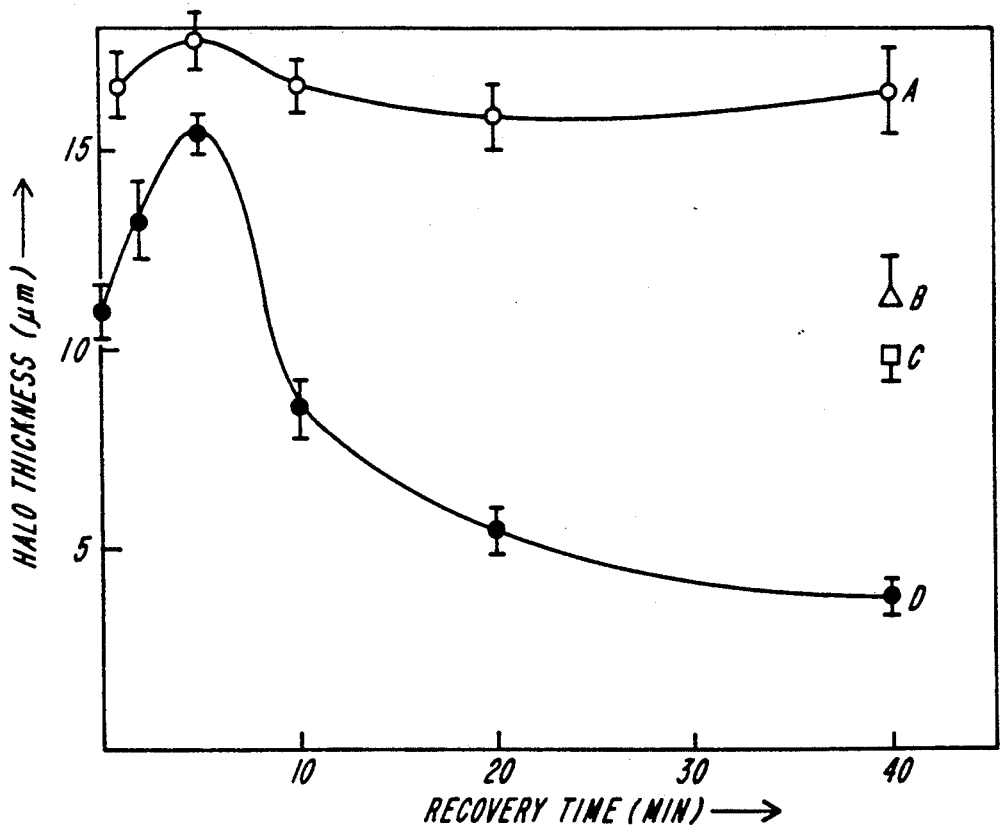
FIG. 7 is a graph of the relationship of halo thickness of nucleoids formed from cells treated with DNA damaging agents and postincubation recovery time: (A) incubation at 0 degrees C in the presence of 3 DNA synthesis inhibitors; (B) incubation at 0 degrees C with no inhibitors; (C) incubation at RT in the presence of 3 inhibitors; and (D) incubation at RT with no inhibitors.

As can be seen in FIG. 7, the halo width is affected by the post treatment incubation time that the cells spend in growth medium, prior to being stripped. A $H_2O_2$ treatment at 0° C, followed by a short period of growth at 37° C. increases the halo size observed upon stripping. A further delay results in the near-complete restitution of the contracted halos. This characteristic increase, then decrease in halo size with growth subsequent to the DNA damaging treatments is precisely what is expected for the operation of the DNA excision-repair activities that are known to exist in mammalian cells. Similar recovery profiles can also be obtained following gamma irradiation (not shown).

Plasmid Preparation:

The 38 kilobase plasmid R6K is grown in *E. coli* (HB101) following Procedures described in Maniatis et al. (*Molecular Clonino: A Laboratory Manual*, Cold Spring Harbor Laboratory, N.Y., (1982) pp. 55–74, herein incorporated as reference). It is purified using a modification of the conventional alkaline extraction procedure of Birnboim (Meth. Enz. (1983) 100:243–255, herein incorporated as reference). This is followed by DNA banding in CsCl containing 600 $\mu$g/ml of EB. The final preparation contains about 15% relaxed circles.

Measuring Abundance of Supercoils:

The plasmid preparation is electrophoresed in Tris-borate buffer essentially according to Serwer Electrophoresis (1983) 4:375–382, herein incorporated as reference) into a 0.2% agarose gel for 80 min at 1.5 volts/cm, then increased the field to 9 volts/cm. Under high field conditions the relaxed circular molecules become "caught" and do not progress further through the gel, while the supercoils and linear molecules migrate further. The fraction of supercoils surviving is estimated by densitometry of the photographic negative.

How Many Chain-Breaks Per Nucleus is Required for Halo Expansion?

The sensitivity of this method is defined by the number of base pairs in the supercoiled unit. In principle, only treatment which introduces chain breaks into a large plasmid DNA and into the DNA loops of the nucleoid halo, at random and at the same rate, can be used to determine the relative number of base pairs in the halo loops and in the plasmid. FIG. 2 schematically compares the supercoiling and relaxation of plasmid DNA with that of the DNA loops of a nucleoid.

Figure 5B:
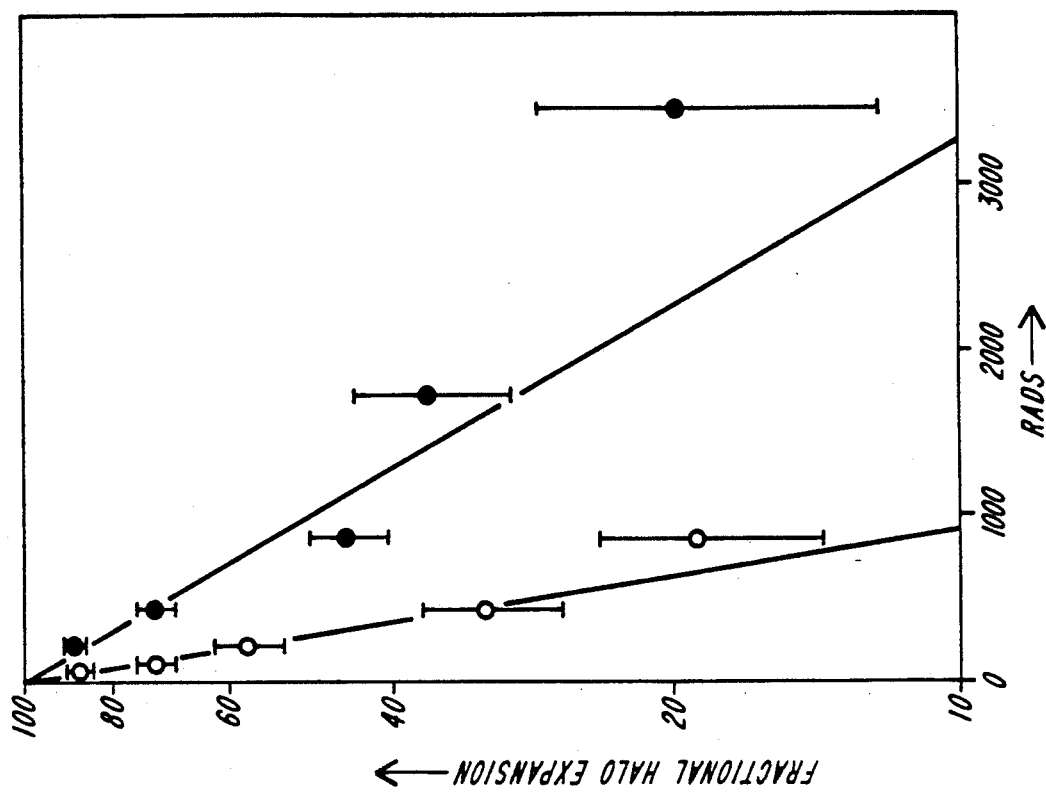
FIG. 5A and 5B are graphs showing the fractional halo expansion and surviving supercoils as measured in the same solution plotted against time of exposure to (A) green light, and (B) gamma radiation.
Figure 5A:
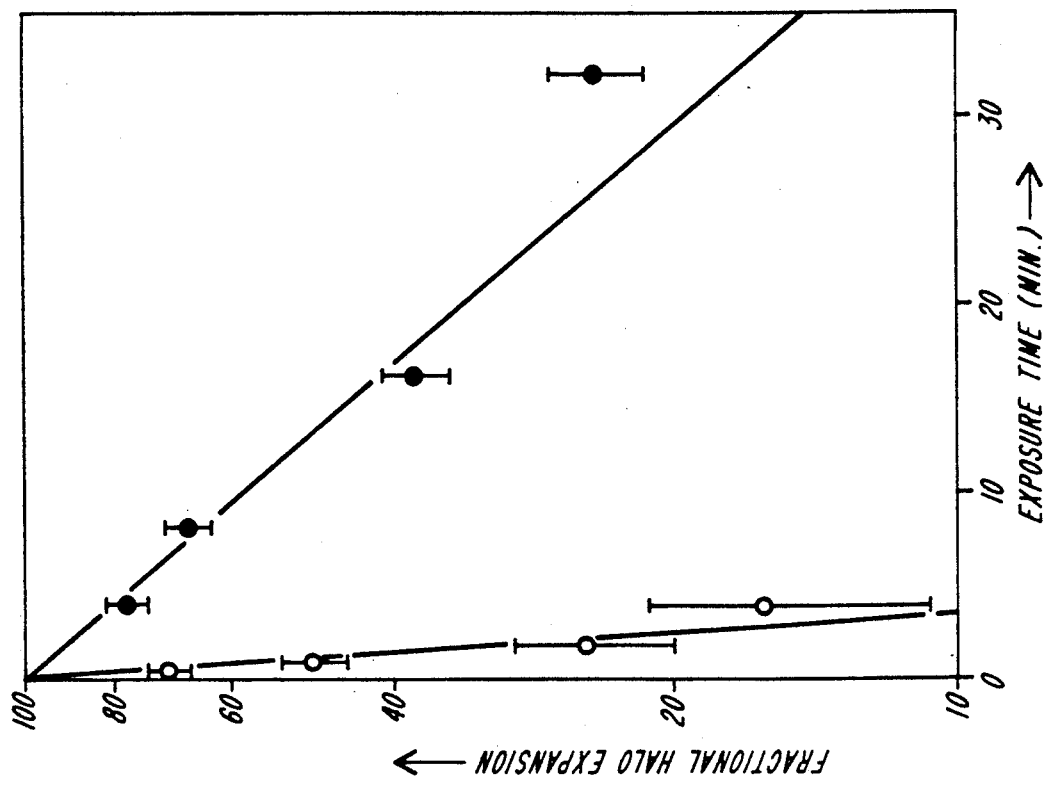

By mixing supercoiled plasmid R6K DNA with the nucleoids in the observation chamber and exposing them to either gamma irradiation or to green light, both halo expansion and the fraction of surviving supercoiled plasmid DNA may be measured in the same solution exposed at the same time. The results are shown in FIGS. 5A and 5B. The halos expand in an exponential fashion with dosage of green light (A) or gamma irradiation (B) and at the same time the fraction of surviving plasmid supercoils diminishes in an exponential fashion. In the case of green light, the halos are 11.6-times more sensitive than the plasmid. In the case of gamma irradiation, the halos are 3.6-times as sensitive as the plasmid. If chain-breakage is the only event responsible for both plasmid relaxation and halo expansion, then the halos are expanded to 63% of their full extension when an average of one chain breakage has occurred for each $(3.6 \times 38,000)$ 137,000 base pairs in the case of gamma irradiation. This corresponds to 37,000 single (or double) strand chain breaks per nucleous of $5 \times 10^9$ base pairs. The limits of detection are approximately 1/10 this value corresponding to the lowest dosage point in FIG. 5B. This corresponds to about 1 break per 1,000,000 bp or 3000 per nucleus. In the case of green light breakage results in a supercoiled unit that is 3.2 times larger.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. A method of measuring chain breakage in the DNA of a eucaryotic cell comprising the steps of:
   (a) contacting said cell with a stripping solution that lyses and solubilizes said cell without denaturing the DNA of said cell, thereby forming a nucleoid having a halo, said halo including undenatured DNA, and having a width related to the number of DNA chain breaks in said loop, and (b) measuring said width of said halo, said width being indicative of said number of chain breaks.

2. The method of claim 1 wherein said determining step is further characterized by comparing said width of said nucleoid halo with a reference value.

3. The method of claim 1 wherein said eucaryotic cell is mammalian.

4. The method of claim 3 wherein said eucaryotic cell is a mammalian cell having substantially low DNA repair abilities.

5. The method of claim 3 wherein said cell is a lymphocyte.

6. The method of claim 1 wherein said contacting step is characterized by treating said cell with a stripping solution having a pH of about 6.0 to 9.0, and comprising a detergent and at least one salt.

7. The method of claim 6 wherein said stripping solution has a pH of about 8.0.

8. The method of claim 6 wherein said stripping solution comprises a nonionic detergent.

9. The method of claim 8 wherein said nonionic detergent is polyoxyethylene ether.

10. The method of claim 9 wherein said stripping solution comprises from about 0.50 to 0.75% polyoxyethylene ether.

11. The method of claim 10 wherein said stripping solution comprises about 0.66% polyoxyethylene ether.

12. The method of claim 6 wherein said stripping solution comprises an ionic detergent.

13. The method of claim 12 wherein said ionic detergent is sodium lauryl sulfate.

14. The method of claim 6 wherein said stripping solution comprises a salt selected from the group consisting of salts of alkali metals, salts of bivalent cations, and combinations thereof.

15. The method of claim 14 wherein said stripping solution comprises about 2 M NaCl, about 10 mM $Mg^{+2}$, and about 0.5 mM $Ca^{+2}$.

16. The method of claim 6 wherein said stripping solution comprises a sugar having a concentration in the range of about 5 to 10% by weight.

17. The method of claim 16 wherein said lysis solution comprises about 7.3% sucrose.

18. The method of claim 1 further comprising the step of pretreating said cell with a DNA repair inhibitor prior to step (a).

19. The method of claim 1 further including prior to step (a) the step of adhering said cell to a support.

20. The method of claim 19 wherein said adhering step is performed by culturing said cell on a glass support.

21. The method of claim 20 wherein said adhering step is further characterized by culturing said cell on a glass coverslip.

22. The method of claim 19 wherein said adhering step is further characterized by pretreating said support with a substance which is capable of binding said cell, and then contacting said pretreated support with said cell.

23. The method of claim 22 wherein said support is pretreated with a cell surface receptor.

24. The method of claim 22 wherein said support is pretreated with an antibody which recognizes said cell.

25. The method of claim 1 further comprising, prior to step (b), the step of increasing the length of said loop of undenatured DNA.

26. The method of claim 25 wherein said increasing step comprises contacting said loop of DNA with a solution comprising urea.

27. The method of claim 25 wherein said increasing step comprises exposing said loop of DNA with an electrostatic field.

28. The method of claim 25 wherein said increasing step comprises exposing said loop of DNA with a hydrodynamic field.

29. The method of claim 19 wherein said support is light transmissive, and said determining step (c) further comprises the steps of:

(a) staining the DNA of said nucleoid with a fluorochrome, said fluorochrome being capable of intercalating between the base pairs of said DNA;

(b) illuminating said stained nucleoid with light capable of exciting said fluorochrome; and (c) determining the halo width of said fluorescent nucleoid.

30. The method of claim 29 wherein said staining step is characterized by contacting said nucleoid with a staining solution containing said fluorochrome, said solution having a pH of about 6.0 to 8.0.

31. The method of claim 30 wherein the pH of said staining solution containing said fluorochrome is about 7.5.

32. The method of claim 29 wherein said fluorochrome is ethidium bromide.

33. The method of claim 29 wherein said fluorochrome is propidium diiodide.

34. The method of claim 31 wherein said staining solution further comprises at least one salt and a buffer.

35. The method of claim 34 wherein said salt includes about 2 M NaCl and about 5 mM $Mg^{+2}$, said buffer includes about 10 mM Tris, and said fluorochrome comprises up to about 100 ug/ml ethidium bromide.

36. The method of claim 29 wherein said illuminating step is carried out by illuminating said stained nucleoids with light having a wavelength of about 510 -560 nm (green light).

37. The method of claim 29 wherein said illuminating and measuring steps are carried out with the use of an epifluorescence microscope, said microscope having measuring means therein.

* * * * *

UNITED STATES PATENT AND TRADEMARK OFFICE
CERTIFICATE OF CORRECTION

PATENT NO. : 5,006,460

DATED : April 9, 1991

INVENTOR(S) : Thomas, Jr. et al.

It is certified that error appears in the above-identified patent and that said Letters Patent is hereby corrected as shown below:

Column 3, line 49, after "about 10" add --mM $Mg^{+2}$,--.

Column 3, line 54, after "contacted" add --if--.

Column 6, line 59, replace "0 5" with --0.5--.

Column 7, line 34, after "(pH7.5),2" add --mM $Mg^{++}$--.

Column 7, line 48-49, after "hydroxyurea; 100" add --µM arabinofuranosyl cytosine (AraC); and 40--.

Column 8, line 48, replace "109" with --$10^9$--.

Signed and Sealed this

Thirtieth Day of March, 1993

Attest:

STEPHEN G. KUNIN

*Attesting Officer*          *Acting Commissioner of Patents and Trademarks*